(12) United States Patent
Willoughby et al.

(10) Patent No.: US 8,764,717 B2
(45) Date of Patent: Jul. 1, 2014

(54) SEAL FOR AN OSTOMY APPLIANCE

(75) Inventors: Alastair Willoughby, Cambridge (GB); Thomas Bates Jackson, Great Chesterford (GB); Gary Stacey, Cambridge (GB)

(73) Assignee: Coloplast A/S, Humlebaek (DK)

( * ) Notice: Subject to any disclaimer, the term of this patent is extended or adjusted under 35 U.S.C. 154(b) by 8 days.

(21) Appl. No.: 13/505,459

(22) PCT Filed: Nov. 2, 2010

(86) PCT No.: PCT/DK2010/050293
§ 371 (c)(1),
(2), (4) Date: Sep. 5, 2012

(87) PCT Pub. No.: WO2011/050816
PCT Pub. Date: May 5, 2011

(65) Prior Publication Data
US 2012/0323192 A1 Dec. 20, 2012

(30) Foreign Application Priority Data

Nov. 2, 2009 (DK) .................................. 2009 70187

(51) Int. Cl.
*A61F 5/445* (2006.01)
*A61F 5/448* (2006.01)
*A61F 5/449* (2006.01)
*A61F 5/44* (2006.01)

(52) U.S. Cl.
CPC .................. *A61F 5/445* (2013.01); *A61F 5/449* (2013.01); *A61F 5/448* (2013.01); *A61F 5/44* (2013.01); *A61F 5/4408* (2013.01); *A61F 2210/0057* (2013.01)
USPC ........... 604/337; 604/317; 604/327; 604/332; 604/338; 604/339

(58) Field of Classification Search
CPC ......... A61F 5/445; A61F 5/449; A61F 5/448; A61F 5/443; A61F 5/44; A61F 5/4407; A61F 5/4408; A61F 2005/44; A61F 2005/445; A61F 2210/0057; A61B 19/38; A61B 17/3462; A61B 2017/348; A61B 2017/3492; A61B 2017/3407; A61B 2017/3419
USPC ......... 604/337, 317, 327, 332, 335, 336, 338, 604/339, 340, 341, 342, 343, 344
See application file for complete search history.

(56) References Cited

U.S. PATENT DOCUMENTS 3,123,074 A * 3/1964 Turner .......................... 604/332
3,194,238 A * 7/1965 Breece, Jr. .................... 604/329
(Continued)

FOREIGN PATENT DOCUMENTS

| GB | 2041753 | 9/1980 |
|---|---|---|
| GB | 2409978 | 7/2005 |

(Continued)

*Primary Examiner* — Adam Marcetich
(74) *Attorney, Agent, or Firm* — Coloplast Corp., Coloplast A/S; Nick Baumann

(57) ABSTRACT

The present invention relates to a sealing wafer (1) adapted to be arranged in a stoma receiving hole (5) of a base plate (2) comprising an attachment platform extending from an outer edge adapted to be attached to the base plate towards an inner edge defining a through-going hole (17) for receiving a stoma, the sealing wafer further comprising at least a first urging part extending transversely from the proximal surface facing towards the user during use of the attachment platform and wherein the first urging part is resilient in the direction transverse to the proximal surface. This provides a sealing wafer which is particularly suitable for use with a stoma around which the skin has an uneven curvature, such as a retracted stoma wherein the stoma has pulled back resulting in a crater-like area.

10 Claims, 3 Drawing Sheets

(56) References Cited

U.S. PATENT DOCUMENTS

| | | | | |
|---|---|---|---|---|
| 3,822,704 | A | * | 7/1974 | Nolan ............................ 604/339 |
| 4,298,206 | A | * | 11/1981 | Kojima ......................... 277/626 |
| 4,559,048 | A | * | 12/1985 | Steer ............................ 604/338 |
| 5,073,169 | A | * | 12/1991 | Raiken ......................... 604/180 |
| 5,324,083 | A | * | 6/1994 | Vogelsang .................... 285/110 |
| 5,330,455 | A | * | 7/1994 | McKay ......................... 604/339 |
| 5,496,296 | A | | 3/1996 | Holmberg |
| 6,071,268 | A | * | 6/2000 | Wagner ........................ 604/332 |
| 6,210,384 | B1 | * | 4/2001 | Cline ............................ 604/338 |
| 6,312,415 | B1 | | 11/2001 | Nielsen et al. |
| 6,679,866 | B1 | * | 1/2004 | Gunawan ...................... 604/338 |
| 6,764,474 | B2 | | 7/2004 | Nielsen et al. |
| 6,840,925 | B2 | * | 1/2005 | Mishima et al. ......... 604/385.01 |
| 8,419,021 | B2 | * | 4/2013 | Mellander .................... 277/567 |
| 2002/0082570 | A1 | * | 6/2002 | Mishima et al. .............. 604/332 |
| 2004/0260256 | A1 | | 12/2004 | Ciok et al. |
| 2005/0184471 | A1 | * | 8/2005 | Ponce ........................... 277/603 |
| 2006/0184145 | A1 | * | 8/2006 | Ciok et al. .................... 604/338 |
| 2007/0100303 | A1 | | 5/2007 | Gregory et al. |
| 2009/0131893 | A1 | * | 5/2009 | Priest et al. ................... 604/342 |
| 2010/0222754 | A1 | * | 9/2010 | Nishtala et al. ............... 604/328 |
| 2011/0092929 | A1 | * | 4/2011 | Weig ............................ 604/338 |

FOREIGN PATENT DOCUMENTS

| | | |
|---|---|---|
| WO | 9817212 | 4/1998 |
| WO | 9853771 | 12/1998 |
| WO | 9960959 | 12/1999 |
| WO | 2006077381 | 7/2006 |

\* cited by examiner

SEAL FOR AN OSTOMY APPLIANCE

The invention relates to a seal for an ostomy appliance which seals around a stoma.

BACKGROUND

In connection with surgery for a number of diseases in the gastro-intestinal or urinary tract, in many cases, a consequence is that the colon, the ileum or the ureter has been exposed surgically and the patient is left with an abdominal stoma, or, in nephrostomy or ureterostomy, the ureter or a catheter is exposed in the back or the chest region or abdominal region, and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma/ureter/catheter. Also in connection with a fistula, the patient will have to rely on an appliance to collect the bodily material emerging from such an opening.

Ostomy appliances are well known. Such appliances may be two-piece or one-piece appliances. In both types of appliances, an adhesive barrier member (or base plate) is attached to the wearer's abdomen/back/chest. In case of a one-piece appliance, a receiving member or bag is permanently attached to the base plate. In case of a two-piece appliance, the adhesive barrier member forms part of a body side member, and a receiving member or bag is attached releasably to the body side ostomy member for receiving exudates or output from the stoma. When using one-piece appliances, the whole appliance, including the adhesive skin barrier securing the appliance to the skin, is normally removed and replaced by a fresh appliance. When using two-piece appliances, the body side ostomy member is left in place up to several days, and only the receiving member or bag attached to the body side member is replaced. The attachment means for attaching an ostomy receiving bag may for example be a system known per se comprising matching coupling rings or matching flanges and adhesive surfaces engaging with and sealing against a flange area of the body side member.

It is necessary to change the body side member of a two-piece appliance when the centre part of the adhesive wafer has deteriorated to such a degree to allow access of the aggressive exudates to the skin surrounding the stoma, irrespective of the fact that the wafer as such has a much longer wearing time. The access of aggressive exudates to the skin causes skin problems. Frequent changes of the body side member of a two-piece appliance is undesirable due to the irritation of the skin, and the quality of life of the user may be improved and the nuisance of the wearing of an ostomy appliance reduced if the intervals between the changing of body side member can be increased.

The service time of the body side ostomy member depends inter alia on the amount and the aggressiveness of the exudates and of the sealing between the stoma and the body side ostomy member. The sealing depends on the fit to the stoma. Conventionally, only a limited number of standard appliances having holes of different size are available and the user or an assistant must customise the body side member by cutting the edge of the hole to adapt the body side member to the stoma.

When cutting the edge of the hole of an adhesive wafer of a conventional one-piece ostomy appliance for adapting it to the size and shape of a stoma, the cutting is complicated by the fact that in order to secure discretion, for decorative purposes, for providing softness, for low noise generation and comfort the bag is often made from an opaque material or covered and/or provided with a cover or front layer rendering it very difficult, if not impossible for the user or the nurse to observe the stoma area for determining a cutting line, for adaptation of the hole or when applying the appliance.

SUMMARY OF THE INVENTION

In one aspect, a sealing wafer is adapted to be arranged in a stoma receiving hole of a base plate comprising an attachment platform extending from an outer edge adapted to be attached to the base plate towards an inner edge defining a through-going hole for receiving a stoma, the sealing wafer further comprising at least a first urging part extending transversely from the proximal surface facing towards the user during use of the attachment platform, and wherein the first urging part is resilient in the direction transverse to the proximal surface.

This provides a sealing wafer which is particularly suitable for use with a stoma around which the skin has an uneven curvature, such as a retracted stoma where the stoma has pulled back resulting in a crater-like area . . . . Thus, providing a resilient urging part facilitates adaption to any surface level difference and provides a planar attachment platform.

The urging part may be formed in a number of different ways. In one embodiment, it is formed of a sheet which is folded with alternating folds so as to achieve a corrugated shape so that the resilience is achieved through spring-like properties. Alternatively, or additionally, the material of the urging part may in itself be resilient.

Moreover, such a sealing wafer can be used for many different sizes and types of uneven skin surfaces around a stoma, and thus the need to provide many different sealing wafers in order to accommodate many different stomas is significantly reduced.

Typically, the urging part extends annularly around the through-going hole. The through-going hole is preformed in order to facilitate application. This provides a seal against the skin surface around the stoma.

In order to provide an additional seal and prevent the urging part from exposure to output from the stoma, which may reduce the functionality of the urging part, the attachment platform of the sealing wafer may extend in a sealing part through the through-going hole and back past where the urging part extends between the attachment platform and the sealing part.

In order to further reduce the risk of leakage, a sealing rib can be provided on the proximal surface of the attachment platform and extend annularly around the urging part when looking at the proximal surface of the attachment platform.

Typically, the attachment platform is in the shape of a disc, having a relatively large surface area in relation to its thickness. The disc can have many shapes, typically annular and circular, but may also have a squared, triangular or ellipsoidal shape.

In another embodiment of a sealing wafer, a second urging part extends annularly around the first urging part. This allows the sealing further ability to adapt to the topography of the skin.

In another aspect, a base plate is provided. The base plate comprises a central through-going hole for receiving a stoma, wherein the sealing wafer is arranged in the central through-going hole.

In yet another aspect, an ostomy appliance is provided, which comprises a sealing wafer as described above and an ostomy collecting bag attachable to the distal surface of the attachment platform.

Such an ostomy collecting bag may be attached to the distal surface of the attachment platform by, for example, an adhesive coupling or a mechanical coupling. Alternatively, the ostomy collecting bag may be permanently attached during manufacturing by, for example, a weld or glue.

DETAILED DESCRIPTION

Figure 1:
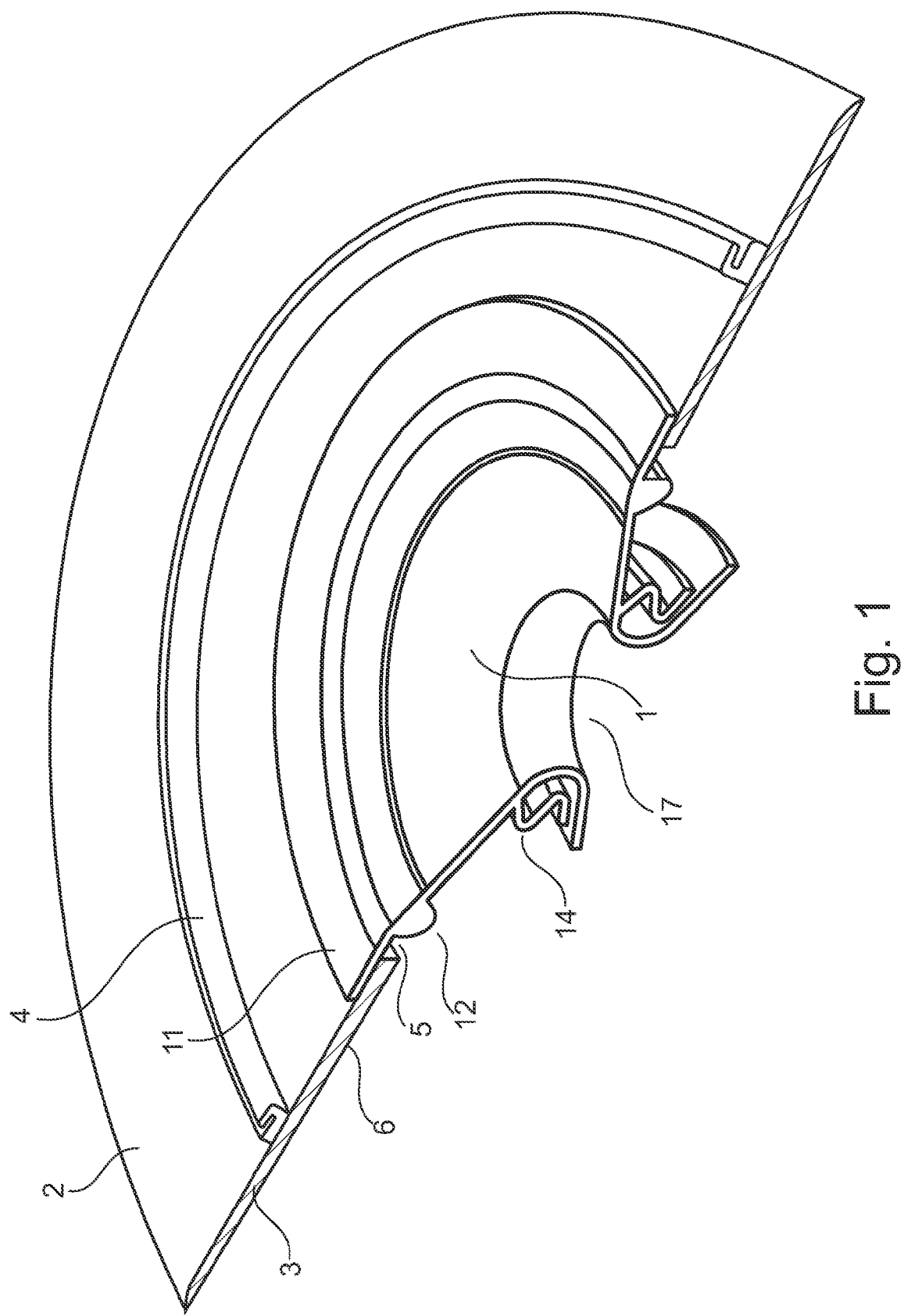
FIGS. 1, 2 and 3 show one embodiment of the sealing wafer according to the invention in section.
Figure 2:
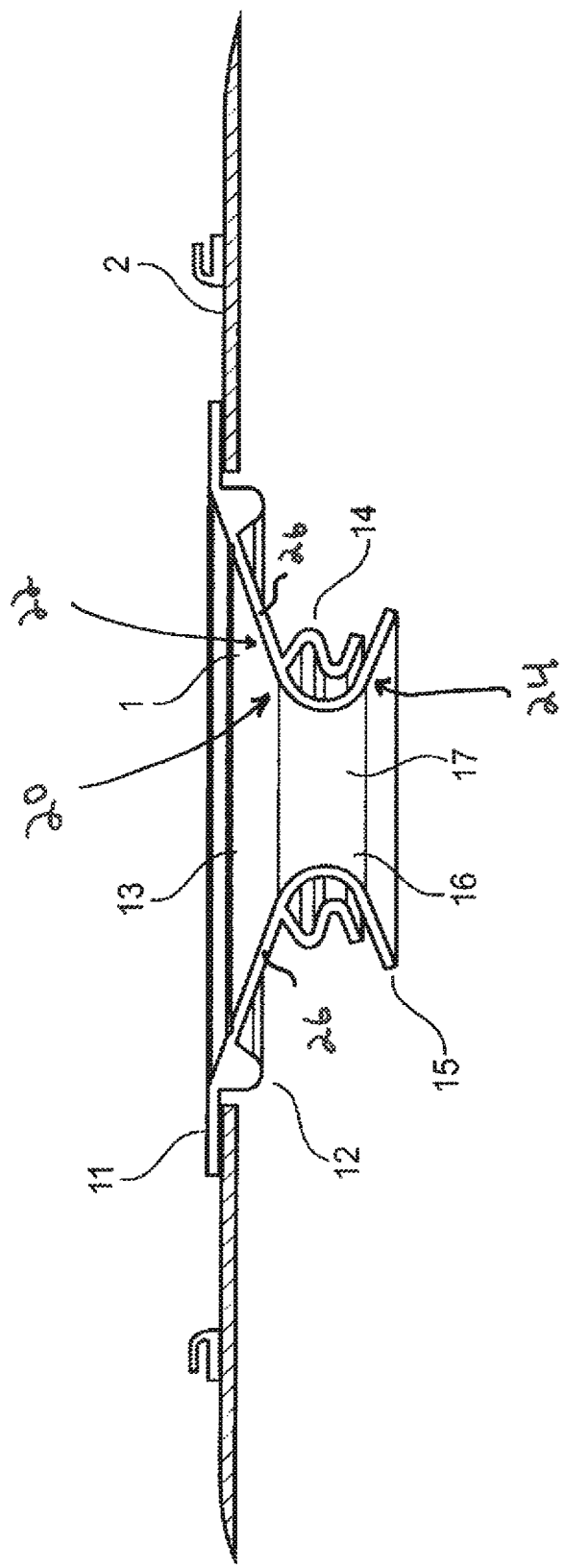
Figure 3:
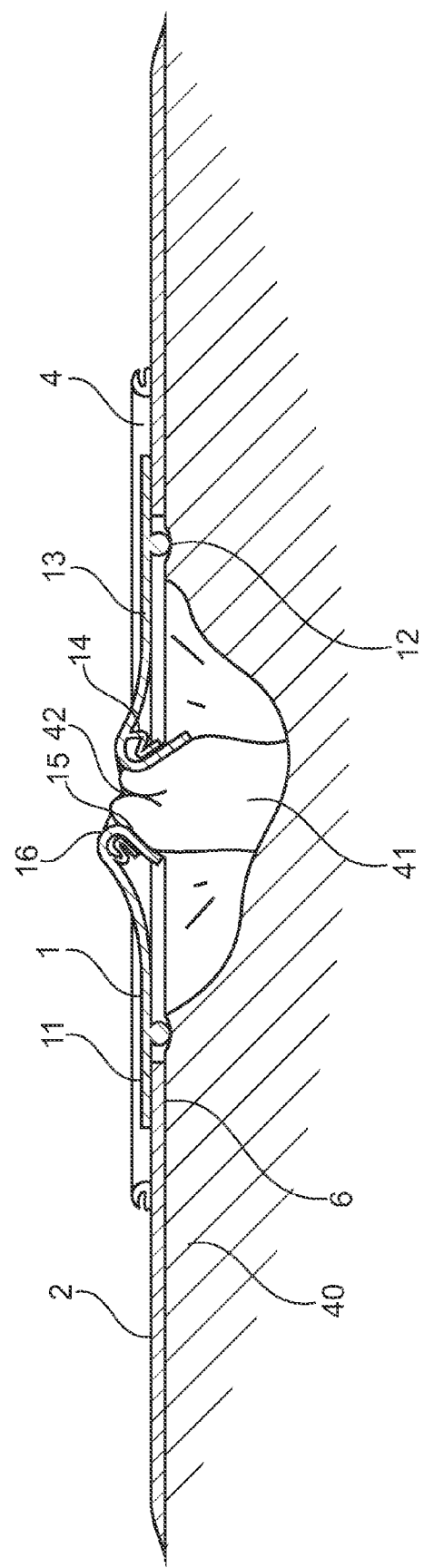

One embodiment of a sealing wafer 1 arranged in an ostomy base plate 2 is shown in FIGS. 1, 2 and 3. The embodiment is shown in section along a symmetry line of both the sealing wafer and the base plate.

The base plate 2 is formed of an adhesive flange 3 whereon a coupling ring 4 is arranged. The coupling ring is attached to the distal side of the adhesive flange 3. Herein, the distal side/surface should be understood as being a part of an element facing away from the body when the ostomy device is placed around the stoma, while any reference to a proximal side/surface should be understood as being part of an element facing towards the body during use. The coupling ring is formed to receive a corresponding coupling ring (not shown) arranged on an ostomy collecting bag (not shown).

The adhesive flange is formed of a backing layer whereon a skin friendly adhesive has been disposed on its proximal side. For simplicity, these elements have not been illustrated but are simply shown in general as the adhesive flange.

A first through-going hole 5 is formed in the centre of the base plate, defined by a first inner edge area 6 of the base plate. The first through-going hole has a size which is large enough to accommodate the sealing wafer and a stoma. Alternatively, the base plate is formed without the first through-going hole. In such cases, the user will cut out a hole in a size and shape especially suitable for the sealing wafer and the individual stoma.

The sealing wafer 1 is arranged in the first through-going hole 5. The sealing wafer is formed of a thermoplastic elastomer (TPE). Such an elastomer may be selected from the group consisting of SEBS, SBS, SIS and TPO (which is a mixture of PP, PE and non cross-linked EPDM rubber). Compared to the base plate, the sealing wafer is very soft and flexible. The sealing wafer will typically have a hardness of 20 Shore A-50 Shore A, and the different elements will have a material thickness ranging from 0.1 mm-2 mm, typically between 0.3 mm-1 mm.

The sealing wafer 1 consists of an elastomeric sheet 13 having an outer periphery defined by an annular flat outer flange 11 and an inner periphery defined orifice surrounding part 16.

A flat outer flange 11 defines the periphery of the sealing wafer. The flat outer flange enables the sealing wafer to be mounted on the inner edge area 6 which defines the first through-going hole 5 of the base plate using conventional methods, such as adhesive or welding.

The elastomeric sheet 13 extends from the inside of this outer flange 11, towards the centre of the ring. The elastomeric sheet is not planar, rather it is frustoconical with the inner part of the sheet closer to the user than the plane of the outer flange when the seal is not deformed under load.

At the centre of the sheet 13, around the axis, there is a re-entrant section 20 of the sheet. This re-entrant section is made up of two regions, a first region 22 and a second region 24. The first region 22 is formed by a wall 26 that continues from the elastomeric sheet 13 and curves towards the user (that is, towards the flange 11) to form an orifice surround 16 around the orifice 17. The second region 24 continues from the end of the orifice surround 16 away from the axis of rotation of the device, for a short distance, and connects to the inner seal 15.

FIG. 3 illustrates how the base plate 2 and the sealing wafer 1 are applied for use. The outer flange 11 is attached to the inner edge area 6 of the base plate. This may be done by the user right before application or may already be done during manufacturing. The base plate 2 is then attached to skin 40 surrounding a stoma 41.

The orifice 17 of the sealing wafer which is defined by the orifice surround 16 is aligned with the stoma so that the inner seal 15 forms a user contacting portion of the seal which sits upon the stoma close to the orifice 42 of the stoma 41. Thus, the orifice 42 of the stoma opens out through the orifice 17 of the sealing wafer 1.

An urging part 14 is formed integrally with the elastomeric sheet. The urging part is made up of a convoluted elastomer part of the same material as the rest of the sealing wafer, located on the elastomeric sheet, so that when the inner seal 15 is deformed in the axial direction towards the elastomeric sheet 13 the urging part 14 will contact the inner seal 15 and provide a force that opposes this deformation.

The urging part 14 provides a resilient buffer between the elastomeric sheet 13 and the inner seal 15. This allows the inner seal to easily conform to the contour of the stoma. The resilience of the urging part is dependent on a number of factors. In particular, by changing the softness of the material and the thicknesses of the urging part, the skilled person is able to achieve a suitable resilience. The choice of resilience will also affect the pressure by which the inner seal 15 pushes against the stoma. The person skilled in the art will understand that the resilience of the urging part should be chosen differently for different users, since the form and type of stomas may vary significantly and thus also the force on which the inner seal 15 is urged onto the stoma should also be varied. However, as a rule of thumb the skilled person would chose a resilience which results in the force exerted on the stoma by the inner seal being less than the diastolic blood pressure in order to reduce the risk of pressure wounds and necrosis.

The overall shape, both profile and thickness, and material of the elastomeric sheet 13, the orifice surround 16 and the inner seal 15 are chosen in such a way, for example as described above, that when a load is applied (steady state or transiently) by the stoma onto the sealing part, the device will maintain the convex profile of the inner surface.

In order to accommodate different sizes of stomas, the sealing wafer may be manufactured with orifice surrounds 16 having different diameters. For example, with a diameter of 10, 15 and 20 mm.

In this embodiment, there is a second outer sealing feature in the form of an elastomeric o-ring 12 that is integrally formed with the elastomeric sheet 13. This outer seal feature is designed to prevent any stoma discharge that may breach the inner seal 15 from reaching the adhesive area of the base plate and causing the entire appliance to lose adhesion to the user.

The elastomeric sheet 13 must be harder and less prone to distortion than the resilient elements 12 and 14. If not, the sealing would flex instead of the resilient elements.

The invention claimed is:

1. A sealing wafer adapted to be arranged in a stoma receiving hole of a base plate, the sealing wafer comprising;
   a wall connected between an annular orifice and a flange, the flange is located on a distal side of the sealing wafer and is adapted to be attached to the base plate, and the annular orifice of the sealing wafer has an interior surface that defines a through-going hole for receiving a stoma;
   an inner seal connected to the annular orifice, the inner seal is located on a proximal side of the sealing wafer such that the annular orifice is located between the flange and the inner seal; and
   an urging part connected to an exterior surface of the wall;
   wherein the urging part is configured to contact an exterior surface of the inner seal when the inner seal is moved in a direction toward the flange, which allows the inner seal to contact a surface of the stoma.

2. A sealing wafer according to claim 1, wherein the urging part extends annularly around an exterior surface of the annular orifice.

3. A sealing wafer according to claim 1, further comprising:
   a seal provided proximal to the flange and disposed annularly around the urging part.

4. A sealing wafer according to claim 3, wherein the flange is in the shape of a disc and the seal is located on a proximal side of the flange.

5. A sealing wafer according to claim 1, further comprising:
   a second urging part disposed annularly around the urging part.

6. A sealing wafer according to claim 1, wherein the base plate includes a central through-going hole for receiving a stoma and the sealing wafer is arranged in the central through-going hole.

7. A sealing wafer according to claim 1, further comprising:
   an ostomy collecting bag attachable to a distal surface of the base plate.

8. A sealing wafer according to claim 7, wherein the ostomy collecting bag is attached to the distal surface of the base plate by an adhesive coupling.

9. A sealing wafer according to claim 7, wherein the ostomy collecting bag is attached to the distal surface of the base plate by a mechanical coupling.

10. The sealing wafer according to claim 1, wherein the inner seal is provided so as to flare away from a central longitudinal axis of the annular orifice.

* * * * *